(12) United States Patent
Hart

(10) Patent No.: US 9,999,417 B2
(45) Date of Patent: Jun. 19, 2018

(54) SUTURE ANCHOR CARTRIDGE

(71) Applicant: KARL STORZ GmbH & Co. KG, Tuttlingen (DE)

(72) Inventor: Rickey Hart, Marco Island, FL (US)

(73) Assignee: KARL STORZ SE & Co. KG, Tuttlingen (DE)

( * ) Notice: Subject to any disclaimer, the term of this patent is extended or adjusted under 35 U.S.C. 154(b) by 164 days.

(21) Appl. No.: 14/846,260

(22) Filed: Sep. 4, 2015

(65) Prior Publication Data

US 2017/0065272 A1  Mar. 9, 2017

(51) Int. Cl.
*A61B 17/04* (2006.01)

(52) U.S. Cl.
CPC ...... *A61B 17/0401* (2013.01); *A61B 17/0485* (2013.01); *A61B 2017/0403* (2013.01); *A61B 2017/0416* (2013.01); *A61B 2017/0427* (2013.01)

(58) Field of Classification Search
CPC ........ A61B 17/0401; A61B 2017/0409; A61B 2017/0414; A61B 2017/0416; A61B 17/0485; A61B 2017/0403; A61B 2017/0427; A61B 17/06114; A61B 17/06133; A61B 17/06138; A61B 2017/06142; A61B 2017/06147; A61B 2017/06152; A61B 2017/06517; A61B 50/00; A61B 30/00; A61B 2050/3007; A61B 2050/3008; A61B 2050/3011; A61B 2050/301; A61B 2050/3009; A61B 2050/3013; A61B 2050/3014; A61B 2050/3015; A61F 2/0811; A61F 2002/0847; A61F 2002/0852
See application file for complete search history.

(56) References Cited

U.S. PATENT DOCUMENTS

| | | | |
|---|---|---|---|
| 5,002,550 A | 3/1991 | Li | |
| 5,078,730 A | 1/1992 | Li et al. | |
| 5,478,345 A | 12/1995 | Stone et al. | |
| 5,741,300 A | 4/1998 | Li | |
| 5,894,921 A * | 4/1999 | Le | A61B 17/0401 206/63.3 |
| 6,022,373 A * | 2/2000 | Li | A61B 17/0401 606/232 |
| 6,200,329 B1 | 3/2001 | Fung et al. | |
| 2010/0023024 A1 * | 1/2010 | Zeiner | A61B 17/0401 606/144 |

FOREIGN PATENT DOCUMENTS

WO  WO 98/10693 A2  3/1998

* cited by examiner

*Primary Examiner* — Katherine M Shi
*Assistant Examiner* — Brooke Labranche
(74) *Attorney, Agent, or Firm* — Muncy, Geissler, Olds & Lowe, P.C.

(57) ABSTRACT

A suture anchor cartridge having a rectangular case portion that includes a top portion and a rectangular bottom portion, the bottom portion including an opening, and the top portion being slidably connected with the bottom portion. A suture anchor is suspended in the opening in the bottom portion. The suture anchor being held at a distal end and at a proximal end by the suture anchor cartridge, and a suture-threading loop is disposed within the bottom portion.

16 Claims, 11 Drawing Sheets

SUTURE ANCHOR CARTRIDGE

BACKGROUND OF THE INVENTION

Field of the Invention

The invention relates to a sterile packaging unit containing a suture threader and a suture anchor for easy application of a suture to the anchor and a method for using the cartridge.

Description of the Background Art

The field of arthroscopy has advanced quickly in recent years, demanding quicker, easier and minimally invasive techniques for increasingly common joint surgeries. Since speed and efficiency translate into quicker recover times and overall better patient experiences, saving time and avoiding mistakes greatly improves operating success.

Soft tissue, such as a tendon or ligament, can rupture and become damaged or detached from a patient's bone as a result of injury or a medical procedure. Injuries of this type include, torn rotator cuffs, labral tears, bicep tendon tears and quadricep ruptures. Surgical treatment of a torn rotator, for example, is designed to reattach the damaged tendon(s) back to the humeral head (ball of the shoulder joint) from which it was torn. Other torn tendons and ligaments require similar procedures.

Bone anchors are one medical implant than can be used to attach soft-tissue to the bone. These anchors are designed to hold the tissue onto the bone at its point of reattachment to allow the tissue to heal and naturally reattach itself to the bone. Alternatively, sutures may be threaded through the soft tissue and tied to an anchor implanted in the bone.

Two points in a normal operation procedure present difficulty and are prone to mistakes. The first is knotting the suture onto the suture anchor or alternatively threading the suture through an eyelet in the anchor. The second is keeping the driver and suture threads in-place and connected to the anchor while adjusting the suture and implanting the anchor in the bone.

After threading the suture through the tendon or ligament to be reattached, the surgeon must tie the suture off to the anchor before inserting the anchor into the bone. Bone anchors are tiny and the holes or mounts to which the suture is tied are even smaller. Therefore, tying the suture off requires extreme dexterity and hand-eye coordination on the part of the surgeon.

One prior art device for aiding the surgeon is disclosed in U.S. Pat. No. 5,741,300 and provides a surface for holding the suture anchor and a threading loop for assisting the surgeon in threading and knotting the suture. The disclosed process, however, still requires threading the loop and knotting the suture to the anchor to prepare the anchor for implantation. Furthermore, the anchor itself is not securely fastened to the holder but simply held by gravity, thus providing the surgeon with little stability beyond the larger holding area.

Knotless suture anchors have been introduced but these present their own difficulties. To provide knotless fastening of the suture, suitable locking bridges are needed between the outer face of the body of the anchor element and the inner face of the sleeve. These make release from this locked position difficult or impossible. Additionally, locking the suture into the anchor requires clamping that can damage the suture by the shearing of the inner screw against the sleeve.

Thus, the prior art devices remain difficult to use and prone to mistakes and damage. The invention described below offers several features to increase usability and efficiency as well as guarantee the safe implantation of the device in the patient. The benefits of these improvements include faster and cleaner surgeries as well as reductions in risk and device malfunction.

SUMMARY OF INVENTION

According to an exemplary embodiment, the suture anchor cartridge includes a rectangular case portion that includes a top portion and a rectangular bottom portion, the bottom portion including an opening, and the top portion being slidably connected with the bottom portion. A suture anchor is suspended in the opening in the bottom portion. The suture anchor being held at a distal end and at a proximal end by the suture anchor cartridge, and a suture-threading loop being disposed within the bottom portion.

According to an exemplary embodiment, both free ends of the suture-threading loop are knotted to the top portion such that the suture-threading loop passes underneath the top portion after the top portion is slid forward. Additionally, the exemplary cartridge is arranged such that the suture-threading loop passes through an eyelet disposed in the distal end of the suture anchor.

An exemplary embodiment of the suture anchor cartridge also provides a slot in the bottom portion aligned with the suture anchor body and terminating at the proximal end of the suture anchor. Additionally, a groove is disposed on the bottom surface of the bottom portion to receive the suture-threading loop. Additionally, a clip is disposed on the bottom of the bottom portion for attachment to a driver shaft.

Furthermore, the cartridge can include a sterile packaging unit with the contents being sterile as well. Accordingly, the rectangular case portion, the suture anchor and the suture-threading loop are sterile.

An exemplary embodiment of the suture anchor includes a distal end that is breakable at a predetermined point, the distal end being held by the suture anchor cartridge. Once broken and separated, the suture anchor is ready for the threading of the suture using the pre-threaded suture threading loop. Once threaded, the suture and suture anchor are no longer connected to the cartridge and are ready for implantation.

Further scope of the applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

DETAILED DESCRIPTION

Figure 1:
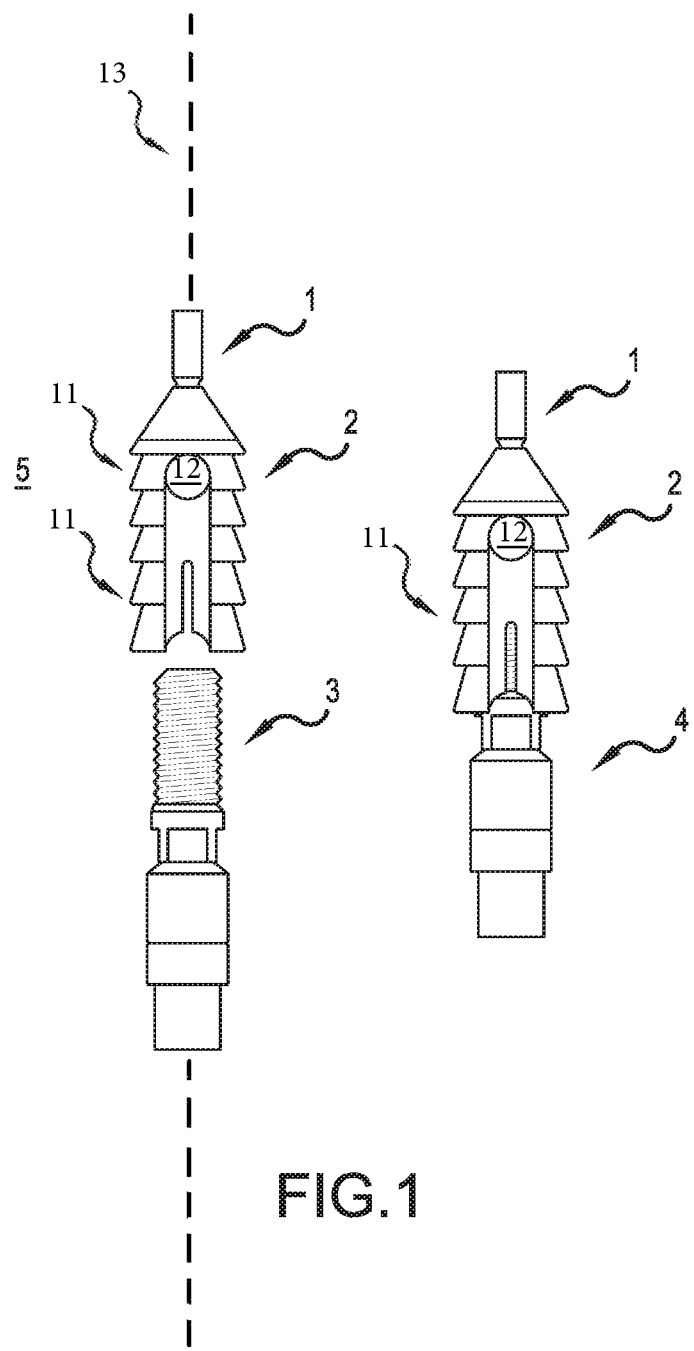
FIG. 1 shows an exploded view of the suture anchor.

In the exemplary design shown in FIG. 1, the suture anchor 5 comprises an inner screw 3, an outer sleeve 2 and a detachable extension 1 for securing the anchor in the cartridge. On the left is a view before insertion of the inner screw and on the right is a view after insertion of the inner screw. The proximal end of the suture anchor provides a square head for insertion into a driver device.

The outer sleeve in this example includes grooves 11 for engaging the bone tissue upon insertion. The head portion 2 of the bone anchor includes an eyelet 12 for receiving the suture thread which extends perpendicular to the longitudinal axis 13 of the screw body.

Figure 2:
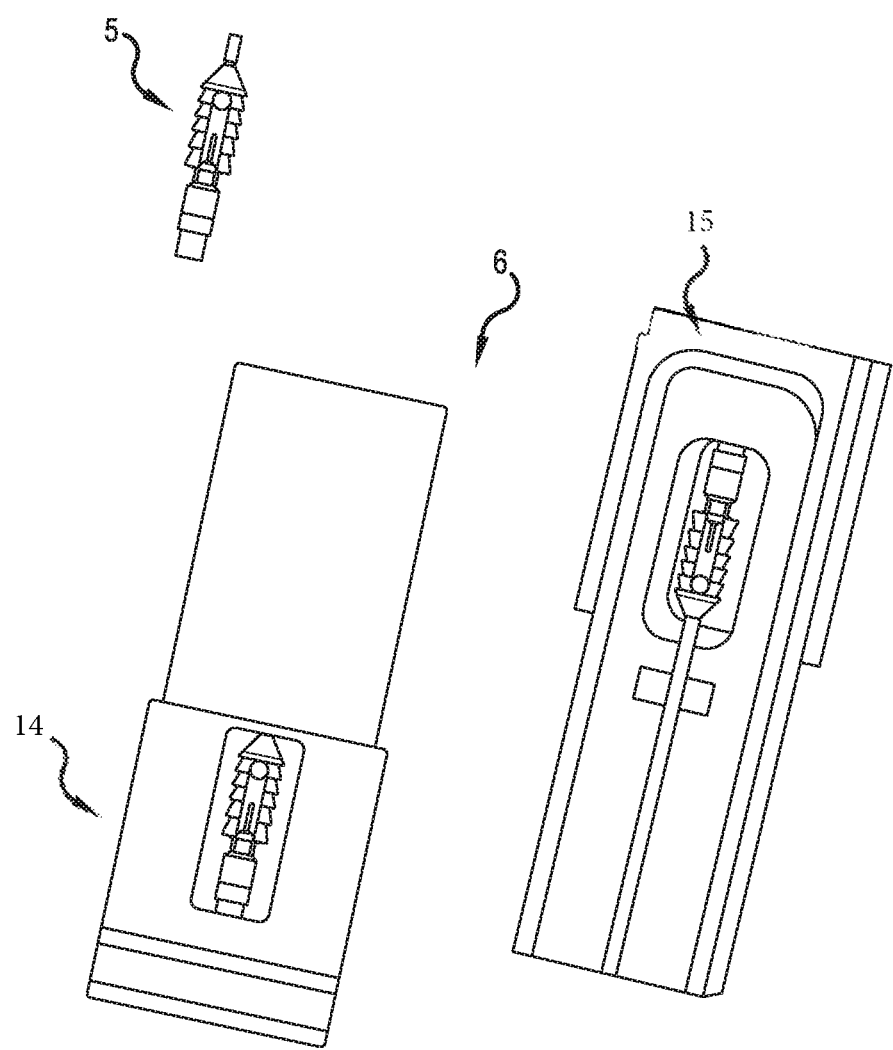
FIG. 2 shows the suture anchor secured in the anchor cartridge.

The suture anchor 5 is also shown in FIG. 2 both inside and outside the cartridge 6. When manufactured, the suture anchor 5 is be provided inside the cartridge along with a pre-threaded loop and surrounded by a sterile packaging unit (not shown). The left view of the cartridge is a top view showing the sliding lid portion 14 and the cartridge body. The right view of the cartridge 6 is an underside view with thread slot (or groove) 15 visible.

In the assembled, ready-to-use state of the cartridge, the suture anchor 5 is positioned within a cartridge cavity that is located centrally within the cartridge 6. Here the suture anchor 5 is secured at its distal end with a short pin-like tip in a wall of the case of the cartridge 6. The suture anchor and the pin-like tip are connected to each other via a predetermined breaking point. The cartridge also contains a laterally located access-opening for viewing and detaching the suture anchor secured within the case.

Figure 3:
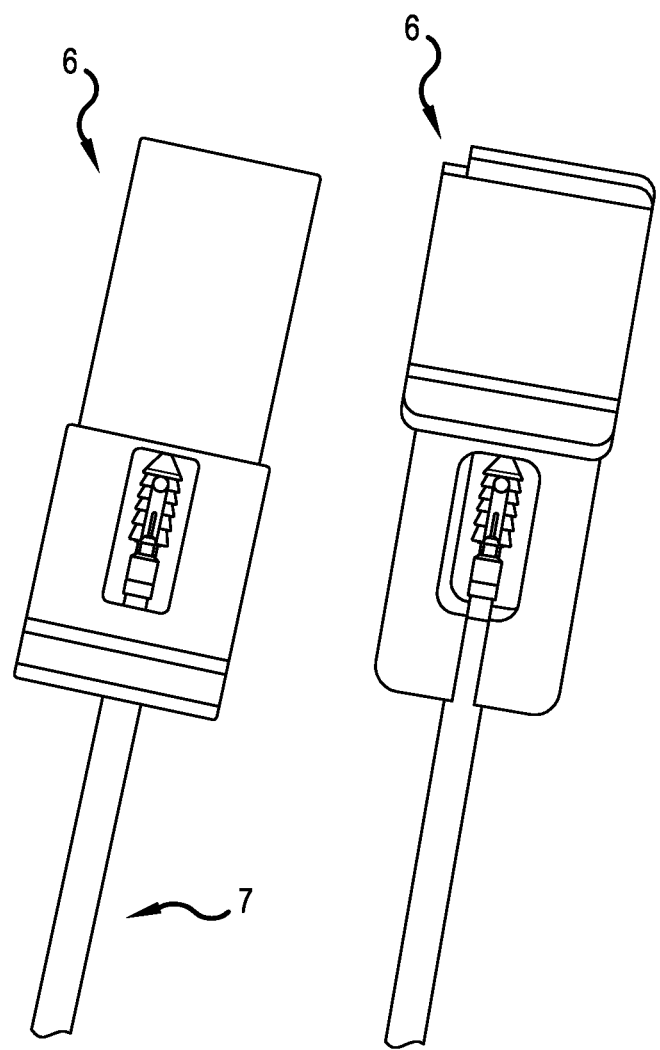
FIG. 3 shows the suture anchor cartridge with driver inserted.

The anchor driver shaft 7 is then inserted into the cartridge 6 as shown in FIG. 3. The driver device 9 can then be pushed forward until its distal end is totally inserted in the lumen of the socket provided by the suture anchor 5. The length of the distal end of the driver device 9 preferably corresponds to the depth of the cavity in the cartridge. Likewise, the tip of the driver shaft 7 is dimensioned with proper depth and width such that it fits snugly on the socket of the bone anchor.

Figure 4:
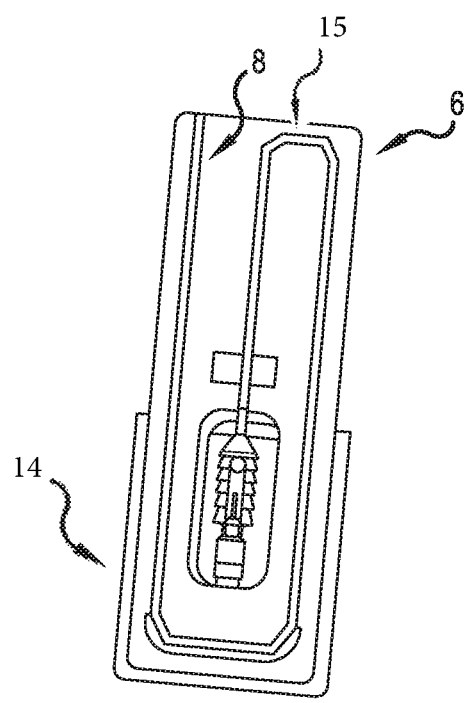
FIG. 4 shows the suture anchor cartridge with pre-threaded suture guiding loop.

The cartridge is provided with a thread 8 that is looped within the cartridge and pre-inserted through the suture anchor eyelet 12. This configuration is shown in FIG. 4. The thread 8 is preferably easier to grip and handle (e.g. thicker, stiffer, more controllable) than the suture itself. Alternatively, the thread 8 could be a thin wire. These materials would allow the surgeon to feed the suture through the loop more easily, and pass the thread back through the suture anchor eyelet 12 once it was detached.

Figure 5:
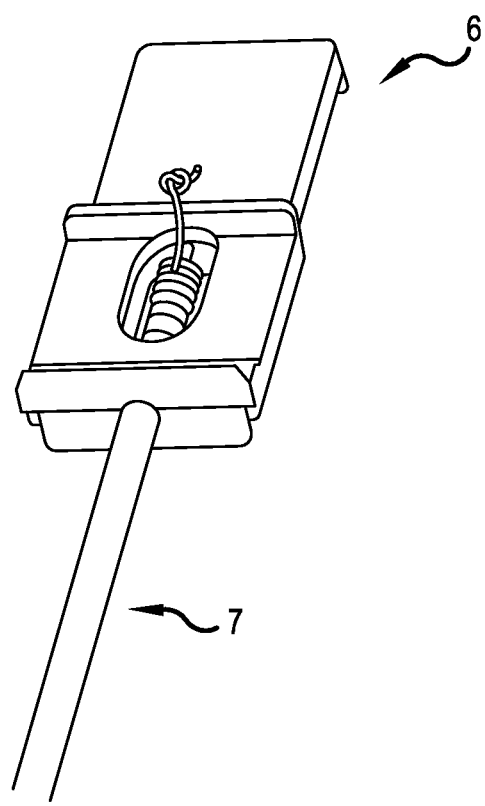
FIG. 5 shows the suture anchor cartridge and where the pre-threaded loop is tied off.

In order to maintain the thread 8 in position through the anchor eyelet 12, both free ends of the thread 8 are knotted to the sliding lid portion 14 of the cartridge when manufactured. This arrangement is shown in FIG. 5. The resulting loop is disposed within the thread slot (or groove) 15 in the bottom portion of the cartridge 6 but not fixed to it.

Figure 6:
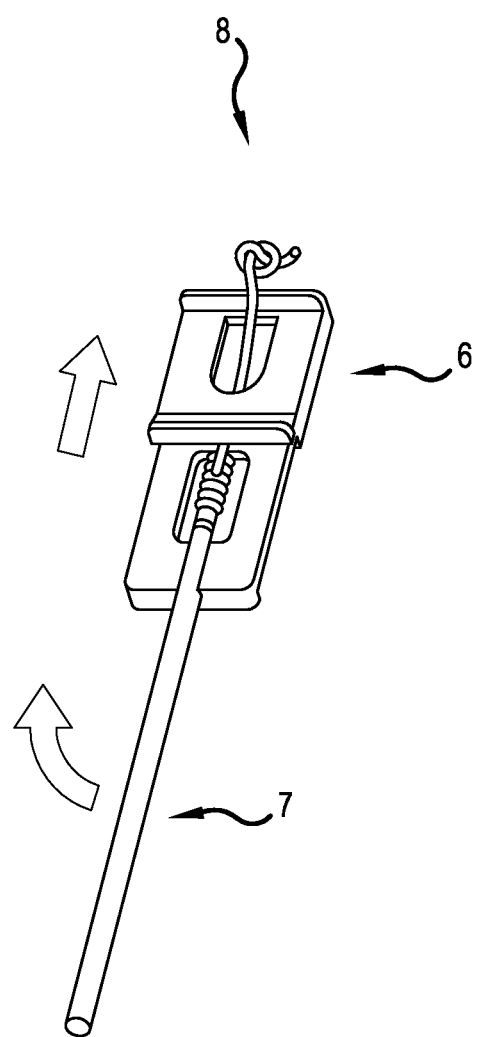
FIG. 6 shows the suture anchor cartridge after sliding the top cover forward.

In the next step, the slidable lid is moved from a proximal position to a distal position as seen in FIG. 6. The suture anchor and the inserted driver device are then exposed. By leveraging out the driver device, the suture anchor preferably breaks at the predetermined breaking point which allows the suture anchor to be removed from the cavity. The driver device and suture anchor now constitute a functional device for a surgery.

Figure 7:
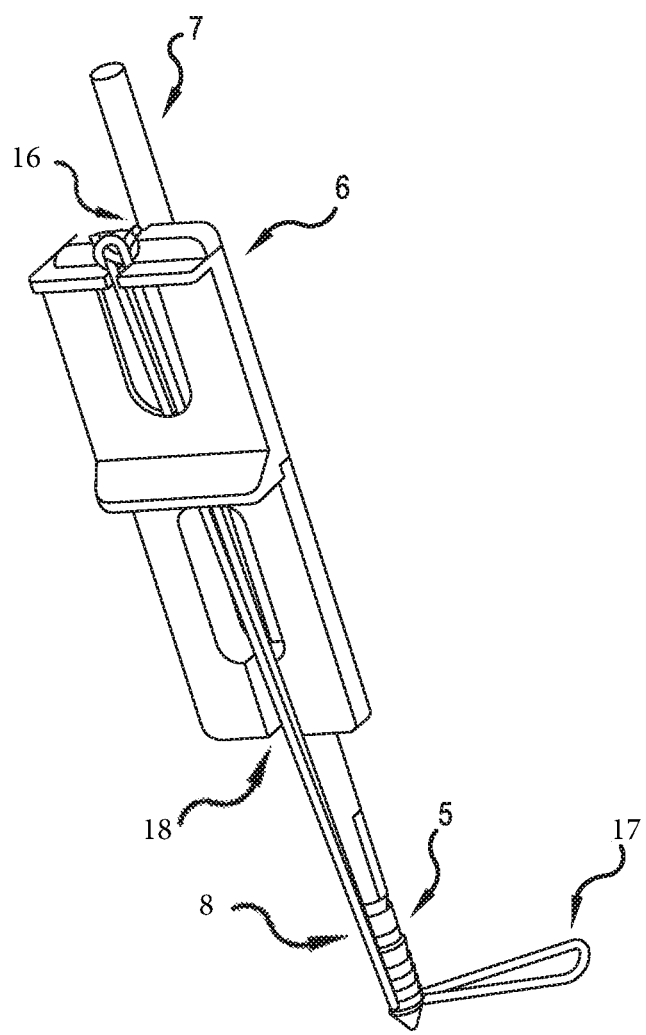
FIG. 7 shows the suture anchor cartridge with the anchor broken out and ready for the suture to be inserted.
Figure 8:
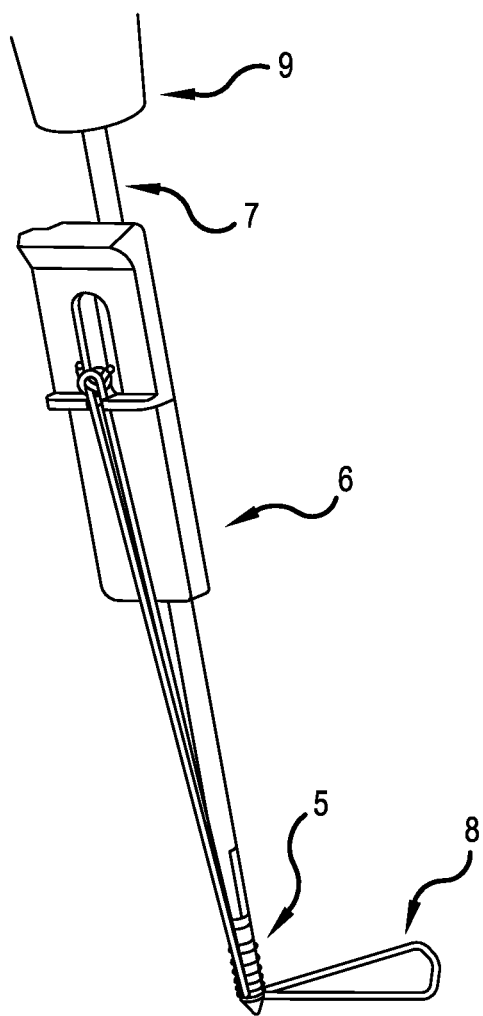
FIG. 8 shows the suture anchor cartridge attached to the driver.

After separation of the driver and anchor from the cartridge, the cartridge can then be clipped via clip 16 onto the shaft of the driver device as shown in FIG. 7. In this position, the cartridge can be moved along the shaft of the driver device. When moving the cartridge proximally, the thread 8 is pulled out from the thread slot (or groove) 15 on the bottom portion. After the separation of the driver and anchor, most of the thread will have been pulled out of the bottom portion of the cartridge leaving a loop 17 outside the anchor eyelet 12. In addition, the slot 18 in the cartridge 6 that held the driver shaft 7 initially is visible in this view.

Figure 9:
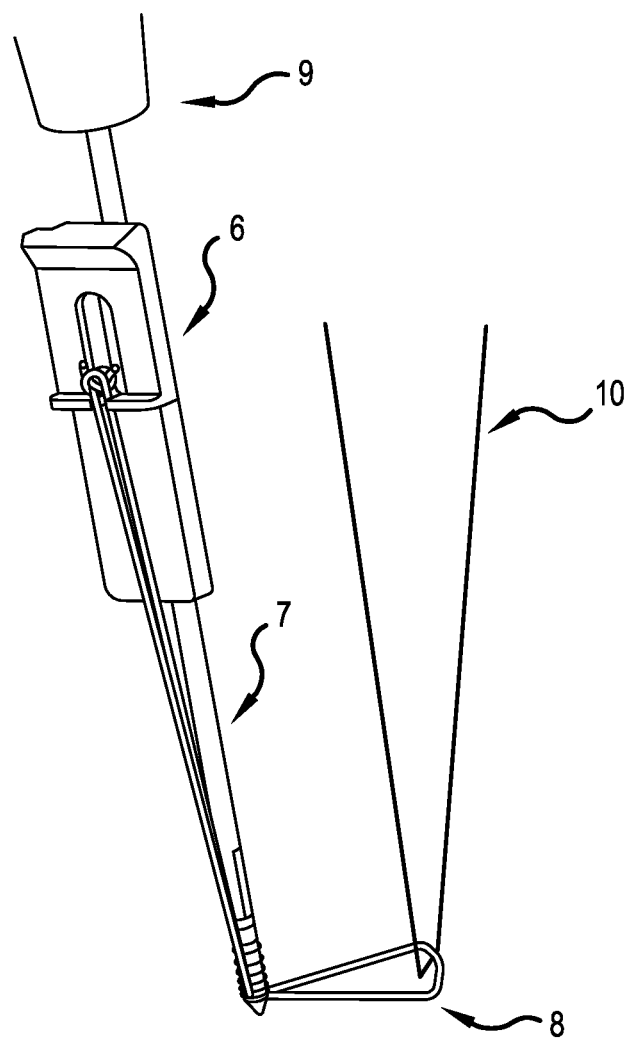
FIG. 9 shows the suture anchor cartridge with a suture inserted into the pre-threaded loop.
Figure 10:
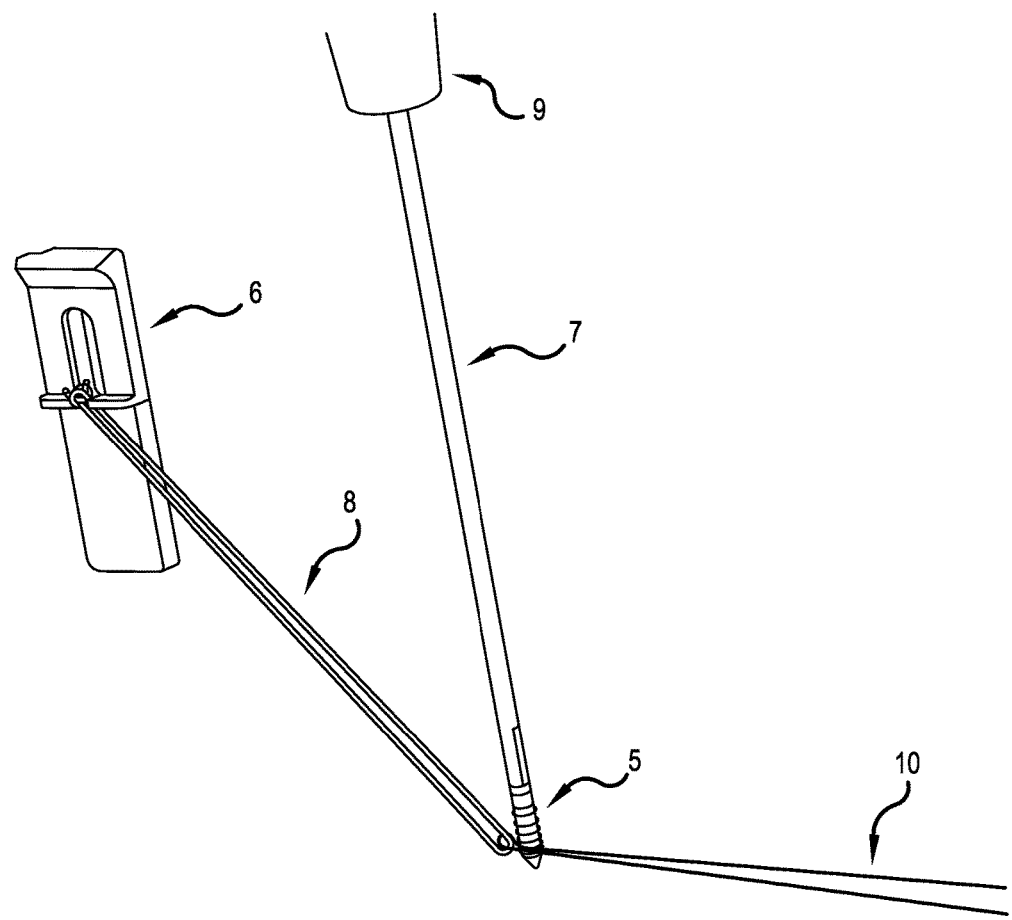
FIG. 10 shows the suture anchor cartridge detached from the driver and drawing the suture through the eyelet of the suture anchor.

The thread and anchor are then usable by the surgeon. The suture 10 is then passed though the loop in the thread 8 as shown in FIG. 9. The cartridge can then be removed or unclipped as shown in FIG. 10. As the cartridge is moved away from the driver and anchor assembly, the suture is drawn through the eyelet. Additionally, if one free end of the suture is held, then the other end of the suture will be drawn through the eyelet.

Figure 11:
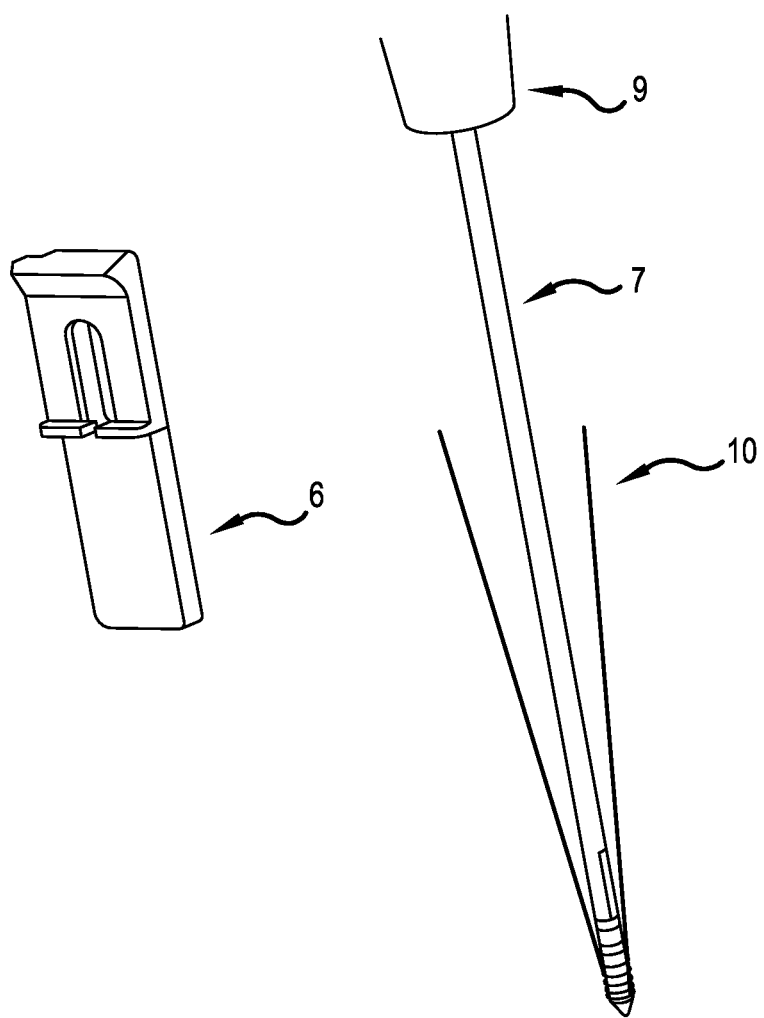
FIG. 11 shows the final result of the method using the suture anchor cartridge with suture threaded and ready for implantation.

Once a free end of the suture is completely drawn through the eyelet, the thread 8 and cartridge 6 assembly are separated from the driver shaft 7, suture 10 and anchor 5 assembly. This final result is apparent in FIG. 11. The threaded suture is then ready for the surgeon to implant the anchor into the bone.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A suture anchor cartridge, comprising:
    a rectangular case, including:
        a rectangular lid portion; and
        a rectangular bottom portion, the bottom portion including an opening, and
    the rectangular lid portion being slidably connected with the bottom portion;
    a suture anchor suspended in the opening in the bottom portion, the suture anchor being held at a distal end and at a proximal end by the suture anchor cartridge; and
    a suture-threading loop disposed within a bottom surface of the bottom portion,
    wherein the rectangular lid portion extends over at least part of a top surface of the bottom portion and along at least two lateral sides of the bottom portion.

2. The suture anchor cartridge of claim 1, wherein both free ends of the suture-threading loop are knotted to the rectangular lid portion.

3. The suture anchor cartridge of claim 2, wherein the suture-threading loop passes underneath the rectangular lid portion after the rectangular lid portion is slid forward.

4. The suture anchor cartridge of claim 2, wherein the suture-threading loop passes through an eyelet disposed in the distal end of the suture anchor.

5. The suture anchor cartridge of claim 1, further comprising a slot in the bottom portion aligned with a body of the suture anchor and terminating at the proximal end of the suture anchor.

6. The suture anchor cartridge of claim 1, further comprising a slot disposed on a bottom surface of the bottom portion which receives the suture-threading loop.

7. The suture anchor cartridge of claim 6, wherein the rectangular case, the suture anchor, and the suture-threading loop are sterile.

8. The suture anchor cartridge of claim 1, further comprising a sterile packaging unit.

9. The suture anchor cartridge of claim 1, wherein the distal end of the suture anchor held by the suture anchor cartridge is breakable at a predetermined point.

10. The suture anchor cartridge of claim 1, further comprising a clip disposed on the bottom surface of the bottom portion for attachment to a driver shaft.

11. The suture anchor cartridge of claim 1, wherein the rectangular lid portion and the bottom portion form the rectangular case, the rectangular case holding the suture-threading loop and the suture anchor.

12. A suture anchor cartridge, comprising:
a rectangular case extending along a longitudinal direction, including:
a rectangular bottom case, the bottom case including a through opening and a thread slot;
a top case extending substantially halfway along the rectangular case, the top case being slidably connected with the bottom case;
a suture anchor held in the through opening of the bottom case, the suture anchor being held at a distal end and at a proximal end by the bottom case portion; and
a suture-threading loop disposed within the thread slot of the bottom portion, the suture threading loop passing though an eyelet in the suture anchor,
wherein both free ends of the suture-threading loop are knotted to the top case portion.

13. The suture anchor cartridge of claim 12, wherein the distal end of the suture anchor held by the bottom case is breakable from the bottom case at a predetermined point.

14. The suture anchor cartridge of claim 12, wherein the bottom case is mountable to a driver shaft of a driver device for insertion of the suture anchor.

15. The suture anchor cartridge of claim 12, wherein the top case extends in a lateral direction beyond the bottom case, the lateral direction being perpendicular to the longitudinal direction.

16. The suture anchor cartridge of claim 12, wherein the top case includes another through opening aligned with the through opening of the bottom case portion.

* * * * *